United States Patent [19]

Bryson, Sr.

[11] Patent Number: 5,281,401
[45] Date of Patent: Jan. 25, 1994

[54] VAPOR DISPENSING SYSTEM

[75] Inventor: John D. Bryson, Sr., Sussex, Wis.

[73] Assignee: Vaportek, Inc., Sussex, Wis.

[21] Appl. No.: 881,754

[22] Filed: May 8, 1992

[51] Int. Cl.⁵ .............................................. A61L 9/00
[52] U.S. Cl. ...................................... 422/305; 422/5;
    422/306; 422/255; 422/325; 422/638; 422/639;
    239/66; 239/70; 261/DIG. 17
[58] Field of Search .................... 422/305–306,
    422/298, 292, 28, 5; 222/3, 4, 6, 152, 153, 255,
    160, 321, 325, 372, 378, 638, 639, 645, 646, 1,
    649; 261/30, DIG. 17, 24; 55/36; 137/511,
    519.5, 587; 239/61, 66, 70

[56] References Cited

U.S. PATENT DOCUMENTS

| | | | |
|---|---|---|---|
| 3,123,249 | 3/1964 | Gorand et al. | 137/587 X |
| 3,923,934 | 12/1975 | Watkins | 261/24 |
| 3,964,685 | 6/1976 | Chauvigne | 239/66 |
| 4,108,601 | 8/1978 | Wolff | 422/295 |
| 4,241,020 | 12/1980 | Grantham | 422/305 X |
| 4,601,886 | 7/1986 | Hudgins | 422/305 X |
| 4,834,265 | 5/1989 | Snyder | 222/1 |

*Primary Examiner*—Robert J. Warden
*Assistant Examiner*—E. Leigh Dawson
*Attorney, Agent, or Firm*—Michael Best & Friedrich

[57] ABSTRACT

A vapor dispensing system comprising a container adapted to contain a cartridge for controllably dispensing a liquid substance as a vapor, a pump for causing a flow of the vapor, conduit means for conveying the vapor flow including a first conduit communicating between the container and the pump, a second conduit communicable between the pump and the atmosphere, and means for controlling the flow of vapor.

3 Claims, 1 Drawing Sheet

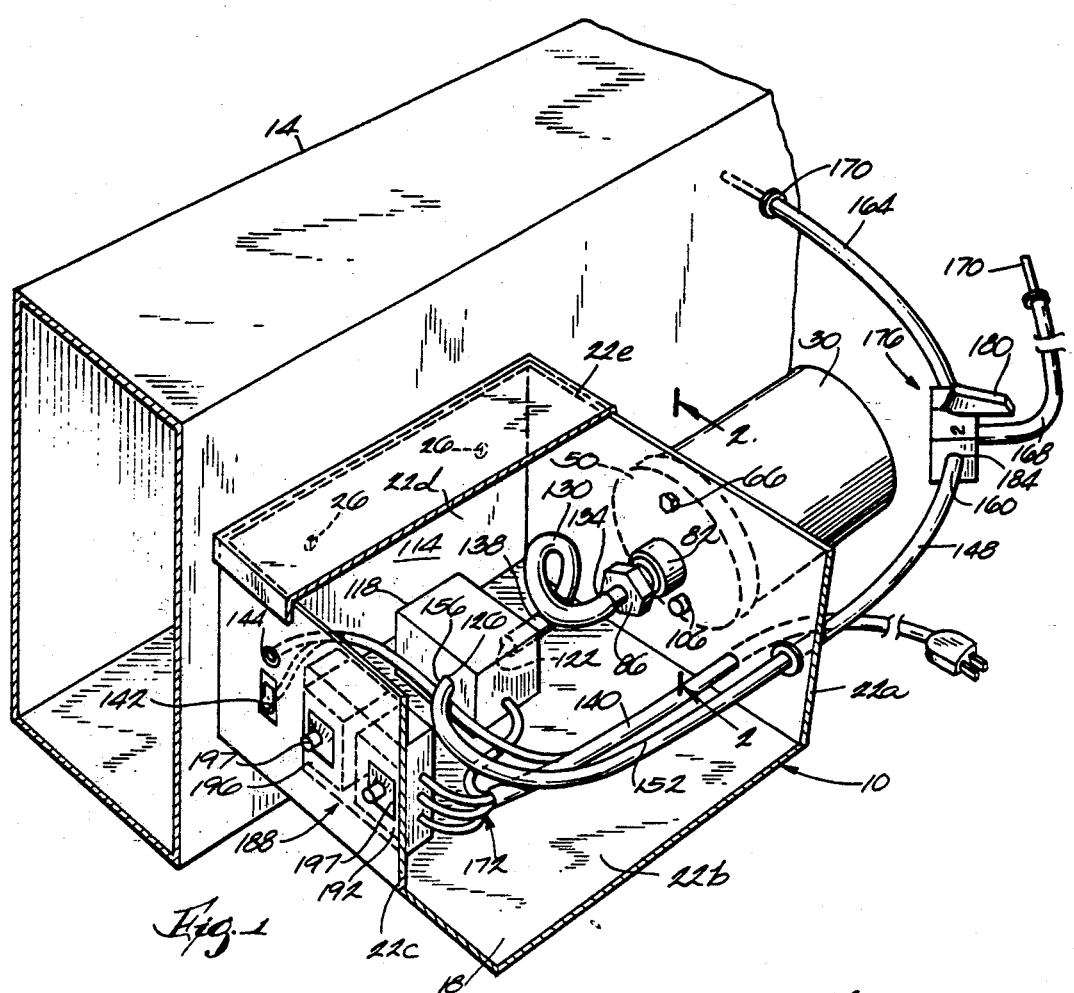

VAPOR DISPENSING SYSTEM

BACKGROUND OF THE INVENTION

1. Technical Field

The invention relates generally to vapor dispensing systems, and more particularly to systems for dispensing a liquid substance as a vapor.

2. Related Prior Art

Attention is directed to the following references:
4,377,399 Bryson Mar. 22, 1983
4,303,617 Bryson Dec. 1, 1981
4,229,415 Bryson Oct. 21, 1980
3,885,737 Watkins May 27, 1975

SUMMARY OF THE INVENTION

The invention provides a vapor dispensing system comprising a container adapted to contain a cartridge for controllably dispensing a liquid substance as a vapor, a pump for causing a flow of the vapor, conduit means for conveying the vapor flow and including a first conduit communicating between the container and the pump, a second conduit communicable between the pump and the atmosphere, and means for controlling the flow of vapor.

The invention also provides a vapor dispensing system comprising a container adapted to contain a cartridge for controllably dispensing a liquid substance as a vapor, dispensing means for pumping the vapor from the container and for conveying the vapor to the atmosphere, and means for controlling the dispensing means including timer means for activating the dispensing means for operation over a period of operational time and for deactivating the dispensing means over a period of non-operational time.

The invention also provides a vapor dispensing system comprising a container adapted to contain a cartridge for controllably dispensing a liquid substance as a vapor, a pump communicating with the container for causing a flow of the vapor, a dispensing conduit for conveying the vapor flow including a first portion having an end communicating with one of the pump and the container, second and third conduit portions communicable with the first conduit portion, and means for selectively and adjustably affording vapor flow through the second and third conduit portions.

Various other features and advantages of the invention will become apparent to those skilled in the art upon review of the following detailed description, claims and drawings.

BRIEF DESCRIPTION OF THE DRAWINGS

FIG. 1 is a perspective view, partially broken away for illustration, of a vapor dispensing system embodying the invention.

FIG. 2 is a cross-sectional view taken along line 2—2 in FIG. 1.

FIG. 3 is an enlarged cross-sectional view taken along line 3—3 in FIG. 2.

FIG. 4 is a schematic diagram illustrating an alternative embodiment of the vapor dispensing system shown in FIG. 1.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

GENERAL DESCRIPTION

Shown in the drawings is a vapor dispensing system 10 for dispensing a liquid substance as a vapor. In the illustrated application, the system 10 is mounted on a ventilation duct 14 and is operable to introduce a flow of vapor, such as an odorant or deodorant, into the duct 14. The system 10 is supported by a frame or box 18 which includes a number of interconnected support walls (denoted as 22a-22e) and which, in turn, is fixed to the ventilation duct 14 by suitable mounting means 26. It should be understood, however, that the frame 18 need not be mounted directly on the ventilation duct 14 for successfully practicing the invention and, as will be described below, can be located remotely from the duct 14.

The system 10 includes a container 30 that is supported by the frame 18 and that is adapted to contain a cartridge or envelope 34 containing, in turn, the liquid substance to be dispensed as a vapor. The container 30 has a generally cylindrical outer wall 38 defining (FIG. 2) an open end 42 and (not shown) a bottom closing the other end of the cylindrical wall 38. As shown in FIG. 2, the cylindrical wall 38 has a radially outwardly turned lip 46 surrounding the open end 42 of the container 30. The cartridge 34 is preferably made of material that is permeable to the liquid to be dispensed so as to contain the liquid and to controllably dispense the liquid as a vapor. While various suitable constructions for the container 30 and cartridge 34 can be successfully used, in the preferred embodiment, the container 30 and cartridge 34 can be constructed in accordance with the disclosure of U.S. Pat. No. 3,885,737 issued on May 27, 1975.

The container 30 is removeably supported on the frame 18 by (FIG. 2) a container support fitting 50 that is fixed to the frame 18 and that cooperates with the outwardly turned lip 46 to hold the container 30. The container support fitting 50 includes a generally circular cover portion 54 having therein a centrally located opening or outlet 58 and having an interlocking portion 62 that extends around the periphery of the cover portion 54 and that engages the lip 46 on the container 30. The container support fitting 50 is fixed to the frame 18 by (FIG. 2) a fastener 66 extending through the cover portion 54 and one of the support walls 22a. In the illustrated embodiment, the fastener 66 is in the form of a nut and bolt assembly, however any suitable fastener can be used.

Preferably, the engagement of the cylindrical outer wall 38 and lip 46 of the container 30 and the container support fitting 50 is a sealed fit such that the container support fitting 50 and container 30 define a substantially hermetically sealed interior space 68 adapted to contain the vapor dispensing cartridge 34. For reasons discussed fully below, the sealed fit between the container 30 and the support fitting 50 should extend around the entire periphery of the open end 42 of the container 30 and should prevent any leakage of air into the container 30 when a vacuum is applied to the interior of the container 30, i.e. when the pressure inside the container 30 is less than the ambient atmospheric pressure. As mentioned above, the container support fitting 50 should removably support the container 30 to afford ready removal and replacement of the container 30 when the cartridge 34 housed therein is spent. While other constructions of the container support fitting 50 could be used to removably support the container 30, in the illustrated embodiment, the container support fitting, including the interlocking portion 62, is made of a resilient plastic that can be resiliently deformed out of the engaged position shown in FIG. 2 so that the interlocking portion 62 and the lip 46 are disengaged thereby affording removal of the container 30 from the support fitting 50. Similarly, the engaging portion 62 can be deformed out of its engaged position to allow a container to be moved into engagement therewith to a sealed and supported position.

The container support fitting 50 also includes a projection 70 that extends from the outlet 58 through an opening 74 in the support wall 22a of the frame 18 and that has an exteriorly threaded portion 78 on the side of support wall 22a opposite the cover portion 54. The projection 70 is generally hollow and has therethrough a bore 80 communicating with the interior of the container 30.

An interiorly threaded locking ring 82 is located on the threaded portion 78 of the projection 70. For reasons explained below, however, the ring 82 is only partially threaded on the projection 70 so that a portion of the locking ring 82 extends beyond the end of the projection 70.

The system 10 also includes an adapter fitting 86 that is fixed to the container support fitting 50 by the engagement of an exteriorly threaded portion 90 and the locking ring 82. The adapter fitting 86 also has a nipple 94 that is adapted to be connected to an air hose or conduit and has therethrough a bore or passage 98 that communicates with the bore 80 in the support fitting projection 70 and, therefore, with the interior of the container 30.

The container support fitting 50 also has extending therethrough (FIG. 2) an inlet 102 that is spaced radially from the outlet 58 and that is aligned with a second opening 104 in the support wall 22a. Extending between the container fitting inlet 102 and the support wall opening 104 is a one-way inlet valve 106 including an inlet tube providing an air inlet passage 110 communicable between the atmosphere and the interior space of the container 30. As shown in FIG. 2, the one-way valve 106 includes a conventional ball-spring valve 111 that is normally biased against a valve seat to close the inlet passage 110 but that is moveable to permit a flow of air from the atmosphere into the interior of the container 30 when the ambient atmospheric pressure exceeds the vapor pressure inside the container 30 by a predetermined threshold pressure difference.

The system 10 also includes dispensing means 114 for pumping vapor from the container 30 and for conveying the vapor to the atmosphere. While various suitable arrangements for the dispensing means 114 could be successfully employed, in the illustrated embodiment, the dispensing means 114 includes a pump 118 that is supported by the frame 18 and that is communicable with the interior of the container 30. The pump 118 is a conventionally constructed, electrically powered pump having an inlet 122 and an outlet 126. In the preferred embodiment, the pump 118 is an aquarium pump commonly used to aerate a tank of water. The pump inlet 122 communicates with the interior of the container 30 through a first conduit 130 having a first end 134 communicating with the pump inlet 122 and a second end 138 connected to the nipple 94 provided by the adapter fitting 86. An electrical power supply cord 140 is operably connected to the pump 118 through an operator control switch 142 and a power indicator lamp 144, both of which are mounted on one of the support walls 22c. As described below, during system operation, the first conduit 130 conveys a flow of vapor between the interior space 68 of the container 30 and the pump inlet 122.

The dispensing means 114 also includes (FIG. 1) a second or dispensing conduit 148 communicating with the outlet 126 of the pump 118 for conveying a flow of vapor to positions located remotely from the pump outlet 126 and from the container 30. In the illustrated embodiment, the dispensing conduit 148 has a first portion 152 extending between a first end 156 communicating with the pump outlet 126 through the supporting wall 22a of the frame 18, and terminating in a second end 160. The dispensing conduit 148 also includes second and third portions 164, 168 that are communicable with the second end 160 of the first portion 152. The second and third portions 164, 168 of the dispensing conduit 148 respectively support outlet fittings 170 which can, as in the case of the embodiment illustrated by FIG. 1, be mounted on the ventilation duct 14 and can extend through an access opening into the duct 14.

In operation, the system 10 generally operates as follows: operation of the pump 118 draws a flow of vapor that has accumulated in the interior of the container 30 through the first conduit 130 into the pump 118. The withdrawal of vapor from the interior space 68 of the container 30 causes a pressure differential between the interior space 68 and the ambient environment which, when such pressure differential reaches the threshold pressure differential, allows the inlet valve 106 to open, thereby affording passage of air into the interior of the container 30.

The flow of vapor drawn from the container 30 to the pump 118 is discharged as a flow of vapor into the first portion 152 of the dispensing conduit 148. The dispensing conduit 148 conveys the vapor flow from the first portion 152 into the second and third portions 164, 168 of the dispensing conduit 148 to the outlet fittings 170 to a location remotely located from the pump 118 which, in the illustrated case, is the ventilation duct 14.

The system 10 also provides means 172 for controlling the dispensing means 114. In one embodiment of the system 10, the control means 172 includes valve means 176 for selectively and adjustably affording vapor flow through the second and third portions 164, 168 of the dispensing conduit 148. While various suitable constructions could be employed, in the embodiment illustrated by FIG. 1, the valve means 176 includes an adjustable valve 180 having an inlet port 184 communicating with the second end 160 of the first portion 152 of the dispensing conduit 148 and outlet ports (not shown) communicating with the second and third portions 164, 168 of the dispensing conduit 148. The adjustable valve 180 can be of conventional construction and is operable to completely shut-off either one of the second or third conduit portions 164, 168 from the first portion 152 of the dispensing conduit 148. The valve 180 also affords an adjustable and proportional division of the vapor flow from the first portion 152 into the second and third portions 164, 168 of the dispensing conduit 148. Preferably, the valve 180 is located exteriorly of the frame 18 to provide easy-access for adjustment of the relative rates of vapor flow through the second and third portions 164, 168 of the dispensing conduit 148.

FIG. 4 illustrates an alternative arrangement of the valve means 176. In that alternative embodiment, the valve means 176 includes a pair of adjustable valves 185 respectively communicating with the first portion 152 of the dispensing conduit 148 and with one of the second and third portions 164, 168 of the dispensing conduit 148. The arrangement of the valve means 176 shown by FIG. 4 affords complete shut-off of vapor flow through the second or third conduit portions 164, 168 as well as a variation of the vapor flow therethrough. It should readily be understood that the arrangement shown by FIG. 4, wherein each conduit portion or branch communicating with the first portion 152 of the dispensing conduit 148 includes a valve can be adapted to include three or more branches with respective adjustable valves communicating therewith in order to serve a plurality of remote locations or spaces.

The vapor flow control means 172 also includes timer means 188 for activating the dispensing means 114 for operation over a period of operational time and for deactivating the dispensing means 114 over a period of non-operational time. While various suitable constructions for the timer means 188 could be employed, in the illustrated embodiment, the timer means 188 includes a first timer 192 (shown schematically in FIG. 1) for activating the pump 118 for operation over a period of operational time during which the pump 118 draws vapor from the container 30, and a second timer 196 (shown schematically in FIG. 1) for controlling a length of non-operational time during which the pump 118 does not operate.

Preferably, the first and second timers 192, 196 are independently operable and adjustable to vary the lengths of operational and non-operational periods over a range of time periods. In order to provide operator-adjustment of the timers 192 and 196, the timer means 188 is mounted on support wall 22c by suitable mounting means (not shown), and includes a pair of rotatable timer control members or dials 197 that extend through the wall 22c and that are readily accessible by an operator. Rotation of control dials 197 adjusts respective timers 192 and 196. While various constructions of timer means 188 could be used, a suitable timer is a solid-state timer manufactured by SSAC, Inc., P.O. Box 1000, Baldwinsville, N.Y.; part no. ESDR424A4.

During non-operational "pump off" or "rest" time periods, the pump 118 is inoperative and vapor from the cartridge 34 accumulates in the container 30. After the period of non-operational time elapses, as determined by the second timer 196, the pump is activated and causes vapor to flow from the container 30 to the duct 14 for the duration of the period of operational or "pump on" time, as determined by the first timer 192. In other words, the respective lengths of operational time periods and non-operational time periods can be independently controlled by the first and second timers 192, 196. The sum total of consecutive operational and non-operational or "rest" time periods constitutes a complete operating cycle of the system 10.

During operation of the system 10, the means 172 for controlling the dispensing means 114 can be adjusted to regulate the amount of vapor dispensed to locations situated remotely of the container 30. First, through adjustment of the timer control members 197 and, therefore, respective timers 192 and 196, the system 10 can be operated to accommodate a variety of demands for the dispensed vapor by providing a flow of vapor over variable periods of time. For example, the length of an operating cycle of the system 10 can be maintained as constant while the lengths of the operational and non-operational time periods are varied independent adjustment of the timers 192, 196. Or, as another example, either one of the operational or non-operational time periods could be adjusted to vary the operational cycle of the system 10. Because the amount of vapor that accumulates in the container 30 during the "rest" periods of non-operational time diminishes as the amount of liquid in the cartridge 34 is spent, the pump timers 192, 196 thus can be adjusted to accommodate the variation in the amount of vapor available in the container 30 for dispensing, and thereby to enable a more uniform discharge of vapor.

Second, through use of the adjustable valve means 176, 180 to control vapor flow rates through the second and third portions 64, 168 of the dispensing conduit 148, the system 10 can serve multiple locations situated remotely of the container 30. In the illustrated arrangement, the supporting frame 18 is located adjacent the ventilation duct 14 served by the system 10. However, after reviewing the specification, it should be clear that the system 10 need not be located adjacent the served location or locations. Rather, the system 10 can readily be used in an application wherein the container 30 and operator controls (i.e. the timer control members 197 and the valves 180 or 185) are readily accessible and wherein the ventilation ducts or other served spaces are situated remotely of the supporting frame 18.

The system 10 is thus operable to dispense the liquid substance contained by cartridge 34 in a precisely controlled manner. The precision in dispensing liquid substance afforded by the system 10 provides advantage in effectively maximizing the operational life of cartridge 34. In some applications, for example, the cartridge 34 can permit relatively excessive amounts of vapor to permeate therethrough when the cartridge 34 contains an ample weight of liquid. Such excessive vapor permeation reduces the period of time over which the cartridge 34 could otherwise be effectively utilized. By controlling the flow of accumulated vapor from the container 30, the system 10 affords an optimum release of vapor according to the need therefore and maximizes the operational life of the cartridge 34.

The precision in dispensing liquid substance afforded by the system 10 also provides advantage in applications wherein precise amounts or weights of the liquid substance are required to be dispensed into a particular space or volume over a particular time period. In some applications, for example, the liquid substance to be dispensed should be introduced to the served space in an amount sufficient to cause a desired effect but in an amount lower than a threshold amount above which the vapor could be detected. The system 10 provides such precise dispensing of the liquid by controlling both the amount of vapor flow into a particular space and by controlling the time period over which the vapor is introduced to the space and allowed to dissipate in the space.

It should be similarly readily understood that the illustrated arrangement of system components is but one of many arrangements of the vapor dispensing system 10 that can be successfully used and thus the invention is not limited to the illustrated arrangement of system components.

Various features of the invention are set forth in the following claims:

I claim:

1. A vapor dispensing system comprising a container, a cartridge located in said container for dispensing a liquid substance as a vapor into said container, a conduit communicable with the atmosphere, an intermittently operable air and vapor mixture pump operably communicating between said container and said conduit for causing a flow of air and vapor mixture from said container to said conduit, one way valve means permitting inflow of air into said container from the atmosphere for mixture with said vapor in response to pump operation and preventing outflow of air from said container, and timer means connected to said pump for intermittently activating operation of said pump over a period of operational time which is variable for deactivating operation of said pump over a period of non-operational time which is variable independently of the variation of said operational time.

2. A system as set forth inc claim 1 and further including a selectively adjustable valve located in said conduit.

3. A system as set forth in claim 2 wherein said conduit includes a first portion communicating with said pump and second and third portions communicating with said first portion and wherein said valve is located in said conduit to adjustably control vapor flow into said second and third conduit portions.

* * * * *